United States Patent [19]

Yamamori et al.

[11] Patent Number: 5,462,936
[45] Date of Patent: * Oct. 31, 1995

[54] BENZOTHIAZEPINE DERIVATIVES

[75] Inventors: Teruo Yamamori, Takarazuka; Hiroshi Harada, Toyonaka; Katsunori Sakai, Osaka; Kazumi Iwaki, Higashiosaka; Kazuki Matsunaga, Suita, all of Japan

[73] Assignee: Shionogi & Co., Ltd., Osaka, Japan

[*] Notice: The portion of the term of this patent subsequent to Jan. 3, 2012, has been disclaimed.

[21] Appl. No.: 292,226

[22] Filed: Aug. 22, 1994

Related U.S. Application Data

[62] Division of Ser. No. 960,851, Oct. 14, 1992, Pat. No. 5,378,698.

[30] Foreign Application Priority Data

Oct. 21, 1991 [JP] Japan .................... 3-302348

[51] Int. Cl.⁶ .................... A61K 31/55; C07D 417/06
[52] U.S. Cl. .................... 514/211; 540/491
[58] Field of Search .................... 540/491; 514/211

[56] References Cited

U.S. PATENT DOCUMENTS

| | | | |
|---|---|---|---|
| 3,075,967 | 1/1963 | Krapcho | 260/293.3 |
| 4,567,175 | 1/1986 | Takeda et al. | 514/211 |
| 4,584,131 | 4/1986 | Floyd et al. | 260/239.3 B |
| 4,594,342 | 6/1986 | Takeda et al. | 514/211 |
| 4,879,289 | 11/1989 | Zobrist et al. | 514/211 |
| 4,963,545 | 10/1990 | Zorfrist et al. | 514/211 |
| 5,001,236 | 3/1991 | Borcherding et al. | 340/491 |
| 5,063,225 | 11/1991 | Clemence et al. | 514/211 |

FOREIGN PATENT DOCUMENTS

| | | |
|---|---|---|
| 0283310 | 9/1988 | European Pat. Off. |
| 0394101 | 10/1990 | European Pat. Off. |
| 0429060 | 5/1991 | European Pat. Off. |
| 0433683 | 6/1991 | European Pat. Off. |

Primary Examiner—Philip I. Datlow
Attorney, Agent, or Firm—Wenderoth, Lind & Ponack

[57] ABSTRACT

A compound of the formula:

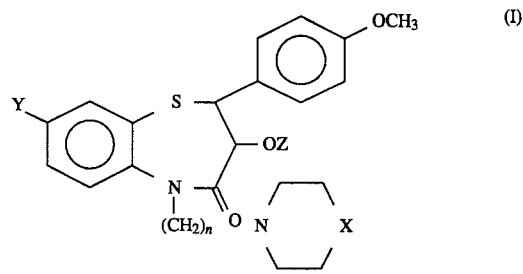

wherein X is $=N-A-R^1$ or $=C(R^1)R^2$; A is a single bond, polymethylene or $-CO-$; $R^1$ and $R^2$ are each hydrogen, $C_{1-6}$ alkyl, $C_{3-7}$ cycloalkyl, unsubstituted or substituted phenyl, optionally substituted benzhydryl, or optionally substituted 5 to 6 membered heterocyclic group; Y is hydrogen, halogen, $C_{1-6}$ alkyl, $C_{3-6}$ cycloalkyl, $C_{1-6}$ alkoxy, optionally substituted phenoxy, optionally substituted benzyloxy, or optionally substituted benzyl; Z is hydrogen or acyl; n is an integer of from 2 to 6, and pharmaceutically acceptable salt thereof. A pharmaceutical composition containing the compound, which is useful for treating hypertension and cardiac diseases, is also provided.

9 Claims, No Drawings

BENZOTHIAZEPINE DERIVATIVES

This application is a division of application Ser. No. 07/960,851, filed Oct. 14, 1992, now U.S. Pat. No. 5,378,698.

The present invention relates to novel benzothiazepine derivatives. In more particular, the invention relates to 5-(piperidinylalkyl or piperazinylalkyl)benzothiazepine derivatives useful as Ca-antagonist as well as coronary vasodilator.

U.S. Pat. No. 3,562,257 discloses benzothiazepine derivatives useful as coronary vasodilator. Although other benzothiazepine derivatives, such as dilthiazem derivatives, are disclosed in U.S. Pat. No. 4,584,131 and Japanese Patent Publication (not-examined) No. 292271/1989, a particular group of benzothiazepine derivatives, i.e., 5-(piperidinylalkyl or piperazinylalkyl)benzothiazepines of the present invention, which are useful as coronary vasodilator and also Ca-antagonist, i.e., cardiac muscle-protector, have not been reported.

It is well known that contraction of cardiac muscle or vascular smooth muscle is associated with Ca-penetration into cells. Thus, the administration of Ca-antagonist to patients results in suppression of cardiac contraction and coronary vasodilation, and therefore, Ca-antagonist is useful as a therapeutical agent for cardiac diseases such as angina pectoris, cardiac infarction, and arrhythmia, hypertension, and cerebrovascular contracture. Dilthiazem is extensively used for treatment of angina pectoris and essential hypertension, but has a drawback that suppression of cardiac contraction caused by diltiazem is too drastic. Accordingly, a new medicine free from such drawback has long been desired.

The present inventors have found that a benzothiazepine derivative of the formula (I):

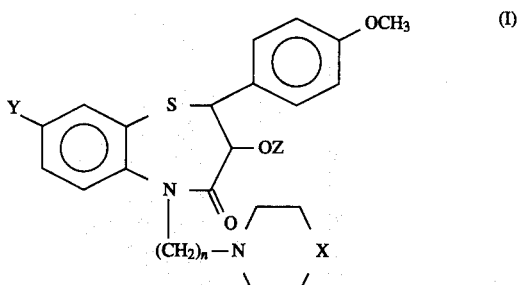

wherein X is $=N-A-R^1$ or $=C(R^1)R^2$; A is a single bond, polymethylene or $-CO-$; $R^1$ and $R^2$ are each hydrogen, $C_{1-6}$ alkyl, $C_{3-7}$ cycloalkyl, unsubstituted or substituted phenyl, optionally substituted benzhydryl, or optionally substituted 5 to 6 membered heterocyclic group; Y is hydrogen, halogen, $C_{1-6}$ alkyl, $C_{1-6}$ cycloalkyl, $C_{1-6}$ alkoxy, optionally substituted phenoxy, optionally substituted benzyloxy, or optionally substituted benzyl; Z is hydrogen or acyl; n is an integer of from 2 to 6, and the pharmaceutically acceptable salt thereof shows excellent vasodilating action on extracted blood vessel and strong protecting action on ischemic cardiac muscle when cultured cardiac cells are used. The inventors have also found that the compound of the formula (I) shows only a slight suppressing action on cardiac functions, and that the compound of the invention is useful for therapeutic or prophylactic treatment of transient ischemic diseases such as coronary thrombosis, cerebral infarction, and the like, and essential hypertension. The above-identified compound (I) of the invention includes optically active isomers and racemate.

The word "polymethylene" herein used means an alkylene having one or more carbon atoms and includes methylene, ethylene, trimethylene, and tetramethylene.

The word "$C_{1-6}$ alkyl" means a straight or branched chained alkyl having 1 to 6 carbon atoms and it is exemplified by methyl, ethyl, n-propyl, iso-propyl, n-butyl, iso-butyl, sec-butyl, tert-butyl, n-pentyl, iso-pentyl, neo-pentyl, tert-pentyl, 2-methylbutyl, n-hexyl and iso-hexyl.

The word "$C_{3-7}$ cycloalkyl" means a cycloalkyl having 3 to 7 carbon atoms and includes cyclopropyl, cyclobutyl, cyclopentyl, and cyclohexyl.

The word "5 to 6 membered heterocyclic group" means a saturated or unsaturated 5 to 6 membered heterocyclic group containing one or more nitrogen atoms and optionally containing one or more oxygen atoms and/or sulfur atoms in the ring. Specific examples of such heterocyclic group are pyrrolyl, imidazolyl, pyrazolyl, pyridyl, pyridazinyl, pyrimidinyl, pyrazinyl, 1,3,5-triazinyl, 1,2,4-triazinyl, 1,2,3-triazinyl, isoxazolyl, oxazolyl, 1,2,3-oxadiazolyl, 1,2,4-oxadiazolyl, 1,2,5-oxadiazolyl, 1,3,4-oxadiazolyl, isothiazolyl, thiazolyl, 1,2,3-thiadiazolyl, 1,2,4-thiadiazolyl, 1,2,5-thiadiazolyl, 1,3,4-thiadiazolyl, furyl, thienyl, and the like. Pyridyl is preferred among them.

"Halogen" means fluoro, chloro, bromo, or iodo, 10 with fluoro and chloro being preferred.

The word "$C_{1-6}$ alkoxy" means alkyloxy wherein the alkyl moiety may be a straight or branched chain, and includes methoxy, ethoxy, n-propoxy, iso-propoxy, n-butoxy, iso-butoxy, sec-butoxy, tert butoxy, n-pentyloxy, iso-pentyloxy, neo-pentyloxy, sec-pentyloxy, tert-pentyloxy, n-hexyloxy, neo-hexyloxy, iso-hexyloxy, sec-hexyloxy, ter-thexyloxy, and the like.

Substituents on phenyl, benzhydryl, 5 to 6 membered heterocyclic, phenoxy or benzyloxy ring may be one or more selected from a group consisting of $C_{1-6}$ alkyl, $C_{1-6}$ alkoxy, halogen and alkylenedioxy defined above.

The term "acyl" means aliphatic acyl having 2 to 7 carbon atoms such as acetyl, propionyl, butyryl, iso-butyryl, pentanoyl, and hexanoyl, cycloalkylcarbonyl having 4 to 7 carbon atoms such as cyclopropanecarbonyl, cyclobutanecarbonyl, cyclopentanecarbonyl, and cyclohexanecarbonyl, and arylcarbonyl having 7 to 11 carbon atoms such as benzoyl, p-toluoyl, and naphthoyl. Preferable acyl groups are aliphatic acyl such as acetyl and propionyl, cyclopropanecarbonyl, cyclobutanecarbonyl, and benzoyl, with acetyl and propionyl being most preferred.

The compound of the invention represented by the formula (I) may be prepared according to the following reaction scheme.

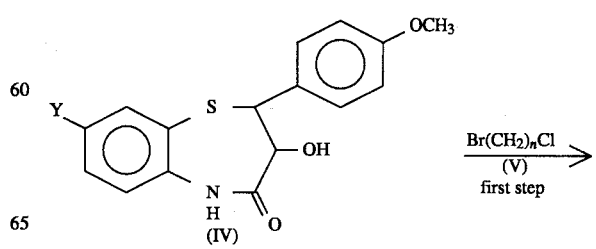

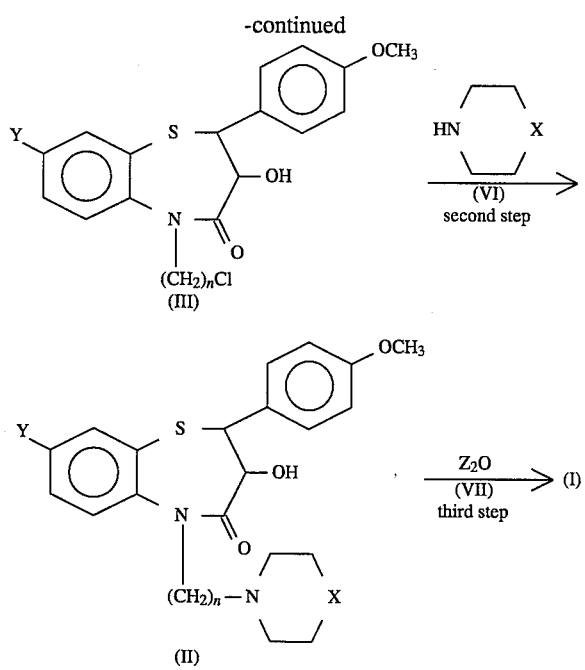

The starting compound (IV) may be prepared according to the method disclosed in Japanese Patent Publication (Examined) No. 43785/1971, Chem. Pharm. Bull., 18 2028, 1970, ibid. 21 92, 1973, etc. The above reaction scheme will be detailed below.

STEP 1

The starting compound (IV) is allowed to react with compound (V) to obtain compound (III). Solvents used for the reaction are alcohols such as methanol, ethanol, propanol, and isopropanol, nitriles such as acetonitrile and propionitrile, hydrocarbons such as benzene and toluene, ethers such as tetrahydrofuran and dioxane, ketones such as acetone and methyl ethyl ketone, amides such as N,N-dimethylformamide and N-methyl-2-pyridone, sulfoxides such as dimethylsulfoxide. Preferred solvents are alcohols, ethers, amides, and nitriles, with isopropanol and acetonitril being most preferred.

Bases used in the reaction may be selected from metal carbonates such as sodium carbonate and potassium carbonate, metal bicarbonates such as sodium bicarbonate and potassium bicarbonate, alkali metal hydride such as sodium hydride and lithium hydride, organic bases such as 1,5-diazabicyclo[4,3,0]non-5-ene and 1,8-diazabicyclo[5,4,0]undec-7-ene. Preferred bases are metal carbonates such as sodium carbonate and potassium carbonate, alkali metal hydride such as sodium hydride. The reaction temperature and reaction time will vary depending on particular base and solvent used. However, the reaction is generally carried out at 0°–120° C., preferably at 0°–80° C., for one hour-four days. When an inorganic base is employed in the reaction, addition of a catalyst amount of pyridines such as 4-dimethylaminopyridine or crown ethers such as 18-crown-6 may accelerate the reaction. The aimed product may be obtained by extracting it with an organic solvent, washing the extract with water, drying the extract over anhydrous magnesium sulfate, and evaporating the solvent. The product may be further purified by means of conventional procedures such as recrystallization, column chromatography, and the like, if desired.

STEP 2

The compound (III) is allowed to react with compound (VI) to obtain compound (II). Solvents used for the reaction are alcohols such as methanol, ethanol, propanol, and isopropanol, nitriles such as acetonitrile and propionitrile, hydrocarbones such as benzene and toluene, ethers such as tetrahydrofuran and dioxane, ketones such as acetone and methyl ethyl ketone, amides such as N,N-dimethylformamide and N-methyl-2-pyridone, sulfoxides such as dimethylsulfoxide. Preferred solvents are alcohols such as methanol, ethanol, propanol and isopropanol, and nitriles such as acetonitrile and propionitrile, with ethanol, isopropanol and acetonitril being most preferred.

Bases used in the reaction may be selected from metal carbonates such as sodium carbonate and potassium carbonate, metal bicarbonates such as sodium bicarbonate and potassium bicarbonate, alkali metal hydride such as sodium hydride and lithium hydride, organic bases such as 1,5-diazabicyclo[4,3,0]non-5-ene and 1,8-diazabicyclo[5,4,0]undec-7-ene. Preferred bases are metal 10 carbonates such as sodium carbonate and potassium carbonate, alkali metal hydride such as sodium hydride. The reaction temperature and reaction time will vary depending on particular base and solvent used. However, the reaction is generally carried out at 0°–120° C., preferably at 0°–80° C., for one hour-four days. When an inorganic base is employed in the reaction, addition of a catalyst amount of pyridines such as 4-dimethylaminopyridine or crown ethers such as 18-crown-6 may accelerate the reaction. The aimed product may be obtained by extracting it with an organic solvent, washing the extract with water, drying the extract over anhydrous magnesium sulfate, and evaporating the solvent. The product may be further purified by means of conventional procedures such as recrystallization, column chromatography, and the like, if desired.

STEP 3

Compound (II) is reacted with compound (VII) to obtain compound (I). Any solvents can be used in the reaction as far as they don't interfere with the reaction. For example, hydrocarbons such as hexane, benzene, toluene, xylene, and cyclohexane, halogenated hydrocarbons such as dichloromethane, chloroform, and 1,2-dichloroethane, ethers, such as ether and tetrahydrofuran, esters such as ethyl acetate may be used. Preferred solvents are halogenated hydrocarbons, with dichloromethane being most preferred.

Bases used in the reaction include organic bases such as triethylamine, pyridine, dimethylaminopyridine, and N-methylmorpholine. A large excess of the base may be employed also as a solvent.

The reaction temperature may range from 0° C. to 80° C., preferably from 0° C. to 50° C. The reaction time varies depending on the reaction temperature, but the reaction will be completed within 1–24 hours, preferably 3–20 hours. The aimed product can be recovered by extracting the product with an organic solvent such as ethyl acetate, washing the extract with water, drying the washed extract over anhydrous magnesium sulfate, and evaporating the solvent from the dried extract. The product may further be purified by conventional procedures such as recrystallization, column chromatography, and the like.

The compound (I) of the invention and pharmaceutically acceptable salt thereof may be used as a therapeutical agent for treating circulatory diseases. The compound and its salt may be formulated into powders, granules, tablets, capsules, injections, and the like, with the aid of pharmacologically acceptable carriers, exipients, and diluents, and they may be orally or parenterally administered to patients. The dosage varies depending on conditions of a particular patient and administration route. In general, however, the daily dosage will vary from 1 mg to 1000 mg, preferably from 1 mg to 100 mg, when orally administered, and it varies from 0.1 to 100 mg, preferably from 0.5 to 30 mg when intravenously administered. This dosage may be administered in one or two divided dose depending on the conditions of patients.

The following detailed examples are presented by way of illustration of certain specific embodiments of the invention.

EXAMPLE 1

3-Acetoxy-5-[3-(4,phenyl-1-piperazinyl)propyl] -2,3-dihydro-2-(4-metoxyphenyl)-8-chloro-1,5-benzothiazepin-4(5H)-one (I-1)

(1) 8.395 g (25.0 mmol) of 2-(4-methoxyphenyl)-3-hydroxy-8-chloro-2,3 -dihydro-1,5-benzothiazepin-4(5H)-one (IV-1), 4.723 g (30.0 mmol) of 1-bromo-3-chloropropane (V-1) and 4.146 g (30.0 mmol) of $K_2CO_3$ were dissolved in 168 ml of acetone, and the mixture was refluxed for 20 hours. The reaction mixture was evaporated under reduced pressure to give a residue, which was chromatographed on silica gel to give 10.96 g of cis-2-(4-methoxyphenyl)-3-hydroxy-5-(3- chloropropyl) -8-chloro-2,3-dihydro-1,5-benzothiazepin-4(5H)-one (III-1) from dichloromethane effluent parts. The obtained compound was recrystallized from ethyl acetate to give 9.146 g as colorless prisms in 88.7% yield.
Mp.: 103°–106° C.
Elementary Analysis(%) for $C_{19}H_{19}NO_3SCl_2$:
Calcd.: C, 55.35; H, 4.64; N, 3.40
Found: C, 55.31; H, 4.70; N, 3.38
IR νmax (Nujol): 3452, 1651cm$^{-1}$
NMR (CDCl$_3$)δ: 2.19(2H,m), 2.84(0H), 3.69(3H,m), 4.63(1H,m), 3.82(3H,s), 4.31(1H,d,d), 4.93(1H,d), 6.90–7.75(7H,m).

(2) 412 mg (1 mmol) of the thus obtained compound (III-1) and 324 mg (2 mmol) of 4-phenylpiperazine (VI-1) were dissolved in 4 ml of acetonitrile. To the mixture was added 166 mg (1 mmol) of potassium iodide as a catalyst, and the mixture was refluxed for 16 hours. The reaction mixture was evaporated under reduced pressure to give a residue, which was chromatographed on silica gel to give 440mg of cis-2-(4-methoxyphenyl)-3-hydroxy-5-[3-(4phenylpiperazinyl)propyl] -8-chloro-2,3-dihydro-1,5-benzothiazepin-4(5H)-one (III-1) from ethyl acetate effluent parts. The compound (III-1) thus obtained was recrystallized from n-hexane to give 400 mg as colorless prisms in 74.3% yield.
Mp.: 70°–71° C.
Elementary Analysis(%) for $C_{29}H32ClN_3O_3S$:
Calcd.: C, 64.74; H, 6.00; N, 7.81
Found: C, 64.51; H, 6.04; N, 7.77
IR νmax (Nujol): 3460, 1661, 1251, 1093cm$^{-1}$
NMR (CDCl$_3$)δ: 1.95(2H,m), 2.54(6H,m), 2.88(1H,d), 3.16(4H,m), 3.64(1H,m), 3.82(3H,s), 4.31(1H,d,d), 4.52(1H,m), 4.93(1H,d), 6.88(4H,m), 7.35(7H,m), 7.73(1H, d).

(3) To 5ml of acetic anhydride was added 800 mg (1.5 mmol) of the thus obtained compound (II-1) and the mixture was heated at 100° C. for 3 hours. The reaction mixture was evaporated under reduced pressure to give a residue, which was dissolved in 10 ml of dichloromethane and neutralized with aqueous sodium bicarbonate. The dichloromethane layer was dried over sodium sulfate. The organic layer was chromatographed on silica gel to give 850 mg of the objective compound (I-1) from ethyl acetate effluent parts. A hydrochloride of the thus obtained compound (I-1) was recrystallized from acetone to give 600 mg as colorless granular crystal in 61.3% yield.
Mp.: 143°–146° C.
Elementary Analysis(%) for $C_{31}H_{36}Cl_3N_3O_4S$: Calcd.: C, 56.97; H, 5.51; N, 6.43
Found: C, 57.31; H, 5.66; N, 6.80
IR νmax (Nujol): 3420, 1750, 1684, 1250, 1180cm$^{-1}$
NMR (CDCl$_3$)δ: 1.91(3H,s), 2.4(2H,m), 3.34(4H,m), 3.5(6H,m), 3.83(3H,s), 4.13(2H,m), 5.05(1H,d), 5.12(1H,d), 6.93(2H,d), 7.4(9H,m), 7.76(1H,d).

EXAMPLES 2–16

Substantially in the same manner as in Example 1, the following compounds I-2–I-16 were prepared.

(2) 3-Acetoxy-5-[3-(4-methyl-1piperazinyl)propyl] -2,3-dihydro-2-(4-methoxyphenyl)-8 -chloro-1,5-benzothiazepin-4(5H)-one (I-2)

(3) 3-Acetoxy-5-[3-(4-(2-piridyl)1-piperazinyl)propyl] -2,3-dihydro-2-(4-methoxyphenyl)-8 -chloro-1,5-benzothiazepin-4(5H)-one (I-3)

(4) 3-Acetoxy-5-[3-(4-(2-methoxyphenyl)-piperazinyl)propyl] -2,3-dihydro-2-(4-methoxyphenyl)-1,5-benzothiazepin-4(5H)-one (I-4)

(5) 3-Acetoxy-5-[3-(4-piperonyl)-1piperazinyl)propyl] -2,3-dihydro-2-(4-methoxyphenyl)-8 -chloro-1,5-benzothiazepin-4(5H)-one (I-5)

(6) 3-Acetoxy-5-[3-(4-(3,4 -methylenedioxyphenyl)-1-piperazinyl)propyl]-2,3-dihydro-2 (4-methoxyphenyl)-8-chloro-1,5-benzothiazepin-4(5H)-one (I6)

(7) 3-Acetoxy-5-[3-(4-(2-furoyl)-1-piperazinyl)propyl] -2,3-dihydro-2-(4-methoxyphenyl)-8 -chloro-1,5-benzothiazepin-4(5H)-one (I-7)

(8) 3-Acetoxy-5-[3-(4-(2-methoxyphenyl)-piperazinyl)propyl] -2,3-dihydro-2-(4-methoxyphenyl)-8 -chloro-1,5-benzothiazepin-4(5H)-one (I-8)

(9) 3-Acetoxy-5-[2-(4-phenyl-1piperazinyl)ethyl] -2,3-dihydro-2-(4-methoxyphenyl)-8 -chloro-1,5-benzothiazepin-4(5H)-one (I-9)

(10) 3-Acetoxy-5-[2-(4-(2-methoxyphenyl)-piperazinyl)ethyl] -2,3-dihydro-2-(4-methoxyphenyl)-8 -chloro-1,5-benzothiazepin-4(5H)-one (I-10)

(11) 3-Acetoxy-5-[2-(4-phenyl-1piperizinyl)ethyl] -2,3-dihydro-2-(4-methoxyphenyl)-8 -chloro-1,5-benzothiazepin-4(5H)-one (I-11)

(12) 3-Acetoxy-5-[3-(4-(4-fluorophenyl)-piperazinyl)propyl] -2,3-dihydro-2-(4-methoxyphenyl)-8 -chloro-1,5-benzothiazepin-4(5H)-one (I-12)

(13) 3-Acetoxy-5-[2-(4-(4-fluorophenyl)-piperazinyl)ethyl] -2,3-dihydro-2-(4-methoxyphenyl)-8 -chloro-1,5-benzothiazepin-4(5H)-one (I-13)

(14) 3-Acetoxy-5-[3-(4,4-diphenyl-1piperizinyl)propyl] -2,3-dihydro-2-(4-methoxyphenyl)-8 -chloro-1,5-benzothiazepin-4(5H)-one (I-14)

(15) 3-Acetoxy-5-[3-(4-(4,4'-difluorobenzhydryl) -1-piperazinyl)propyl]-2,3-dihydro-2-(4-methoxyphenyl)-8-chloro-1,5-benzothiazepin-4(5H)-one (I-15)

(16) 3-Acetoxy-5-[3-(4-(4-chlorobenzhydryl)-piperazinyl)propyl] -2,3-dihydro-2-(4-methoxyphenyl)-8 -chloro-1,5-benzothiazepin-4(5H)-one (I-16)

EXAMPLE 17

(2S-cis)-3-Acetoxy-5-[3-[4-(2-methoxyphenyl)-1-piperazinyl)propyl] -2,3-dihydro-2-(4-methoxyphenyl)-8-chloro-1,5-benzothiazepin-4(5H)-one (I-17)

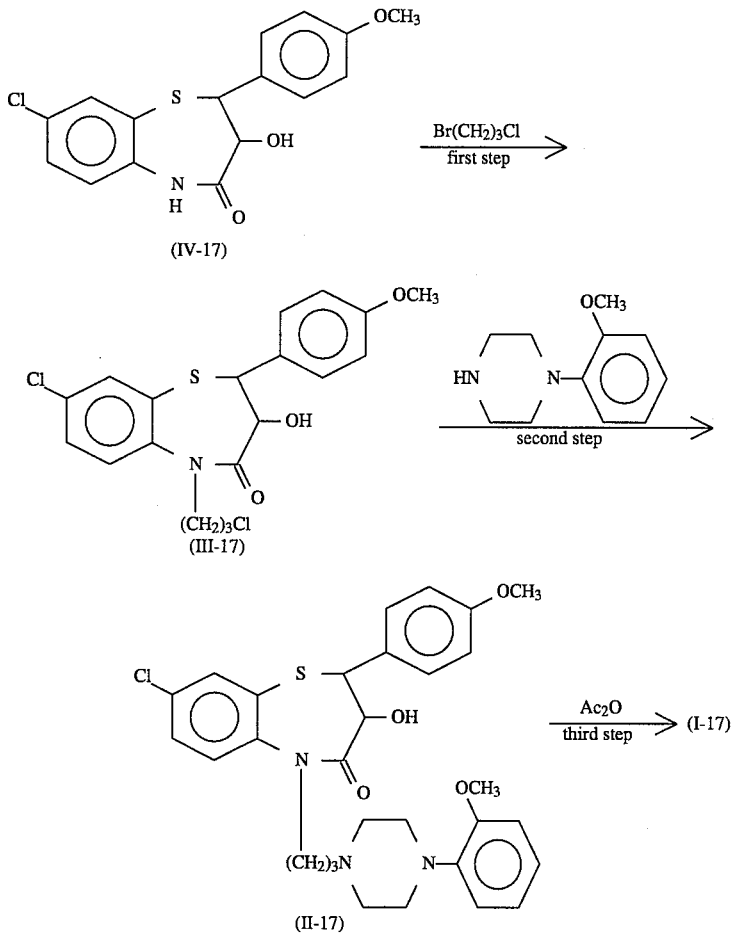

(1) Substantially in the same manner as Example (1), (2S-cis)-2-(4-methoxyphenyl)-3-hydroxy-8-chloro-2,3-dihydro-1,5-benzothiazepin-4(5H)-one as a starting material was treated.

(2) Substantially in the same manner as Example 1, Step 2 and Step 3, 4-(2-methoxyphenyl)piperazine was treated to give the objective compound (I-17) as colorless prisms in 97.0% yield.

Mp.: 109°–111° C. (recrystallization from ethyl acetate)
Elementary Analysis(%) for $C_{32}H_{36}ClN_3O_5S$:
Calcd.: C, 62.99; H, 5.95; N, 6.89
Found: C, 63.09; H, 6.00; N, 6.77
IR vmax (Nujol): 1746, 1678 cm$^{-1}$
NMR (CDCl$_3$)δ: 1.90(2H,m), 1.91(3H,s), 3.85(3H,s), 5.03(1H,d), 3.63(1H,m), 4.47(1H,m), 3.83(3H,s), 5.15(1H, d), 7.28(11H,m)
Specific rotation: [α]D+109.3±1.5 (25° C., c=1.007, MeOH)

EXAMPLES 18–39

Substantially in the same manner as in Example 17, the following compounds 1-18–I-39 were prepared.

(18) (2S-cis)-3-Acetoxy-5-[3-(4-(2-methoxyphenyl) -1-piperazinyl)propyl]-2,3-dihydro-2(4-methoxyphenyl) -8-chloro-1,5-benzothiazepin-4(5H)-one hydrochloride (I-18)

(19) (2S-cis)-3-Acetoxy-5-[3-(4-(2-methoxyphenyl)-1-piperazinyl)propyl]-2,3-dihydro-2-(4-methoxyphenyl)-8-chloro-1,5-benzothiazepin-4(5H)-one phosphate (I-19)

(20) (2S-cis)-3-Acetoxy-5-[3-(4-(2-methoxyphenyl)-1-piperazinyl)propyl]-2,3-dihydro-2-(4-methoxyphenyl)-8-chloro-1,5-benzothiazepin-4(5H)-one citrate (I-20)

(21) (2S-cis)-3-Acetoxy-5-[3-(4-(2-methoxyphenyl)-1-piperazinyl)propyl]-2,3-dihydro-2-(4-methoxyphenyl)-8-chloro-1,5-benzothiazpin-4-(5H)-one fumarate (I-21)

(22) (2S-cis)-3-Acetoxy-5-[3-(4-(4-chlorobenzhydryl)-1-piperazinyl)propyl]-2,3-dihydro-2-(4-methoxyphenyl)-8-chloro-1,5-benzothiazepin-4(5H)-one (I-22)

(23) (2S-cis)-3-Acetoxy-5-[3-(4-(benzhydryl)-piperazinyl)propyl] -2,3-dihydro-2-(4-methoxyphenyl)-8-chloro-1, 5-benzothiazepin-4(5H)-one (I-23)

(24) (2S-cis)-3-Acetoxy-5-[3-(4-(4-dichlorobenzhydryl)-1-piperazinyl)propyl]-2,3-dihydro-2-(4-methoxyphenyl)-8-chloro-1,5-benzothiazepin-4(5H)-one (I-24)

(25) (2S-cis)-3-Acetoxy-5-[3-(4-(4-chlorophenyl)-1-piperazinyl)propyl]-2,3-dihydro-2-(4-methoxyphenyl)-8-chloro-1,5-benzothiazepin-4(5H)-one (I-25)

(26) (2S-cis)-3-Acetoxy-5-[3-(4-(4-methylphenyl)-1-piperazinyl)propyl]-2,3-dihydro-2-(4-methoxyphenyl)-8-chloro-1,5-benzothiazepin-4(5H)-one (I-26)

(27) (2S-cis)-3-Acetoxy-5-[3-(4-(cyclohexyl)-piperazinyl)propyl] -2,3-dihydro-2-(4-methoxyphenyl)-8 -chloro-1, 5-benzothiazepin-4(5H)-one (I-27)

(28) (2S-cis)-3-Acetoxy-5-[3-(4-(2methylphenyl) -1-piperazinyl )propyl ]-2 ,3-dihydro-2-(4methoxyphenyl -8 -chloro- 1,5 -benzothiazepin-4(5H)-one (I-28)

(29) (2S-cis )-3-Acetoxy-5- [3-(4-(4methoxyphenyl) -1-piperazinyl )propyl ]methoxyphenyl -8-chloro-1,5-benzothiazepin-4(5H)-one (I-29)

(30) (2S-cis )-3-Acetoxy-5- [3-(4-(2,4dimethoxyphenyl) -1 -piperazinyl) propyl ]-2,3-dihydro-2-(4methoxyphenyl) -8-chloro-1,5-benzothiazepin-4 (5H) -one ( 1-30 )

(31) (2S-cis )-3-Acetoxy-5-[3-(4-(3,4-dimethoxyphenyl) -1-piperazinyl )propyl]-2,3-dihydro-2-(4methoxyphenyl) -8-chloro-1,5-benzothiazepin-4 (5H) -one ( 1-31 )

(32) (2S-cis )-3-Acetoxy-5-[3-(4-( 3,4,5trimethoxyphenyl) - 1-piperazinyl )propyl]-2,3-dihydro-2-(4methoxyphenyl) -8 -chloro-1,5-benzothiazepin-4 (5H)-one (I-32 )

(33) (2S-cis )-3-Acetoxy-5-[4-( 4-( 2 -methoxyphenyl)-1-piperazinyl)butyl]-2,3-dihydro-2-(4 -methoxyphenyl)-8-chloro-1,5-benzothiazepin-4(5H)-one (I-33)

(34) (2S-cis)-3-Acetoxy-5-[5-(4-(2 -methoxyphenyl)-1-piperazinyl)pentyl]-2,3-dihydro-2-(4 -methoxyphenyl)-8 -chloro-1,5-benzothiazepin-4(5H)-one (I-34)

(35) (2S-cis)-3-Acetoxy-5-[3-(4-(2 -methoxyphenyl)-1-piperazinyl)propyl]-2,3-dihydro-2-(4 -methoxyphenyl)-8 -methoxy-1,5-benzothiazepin-4(5H)-one (I35)

(36) (2S-cis )-3-Acetoxy-5-[ 3-( 4-( 2methoxyphenyl) -1-piperazinyl)propyl]-2,3-dihydro- 2- ( 4 -methoxyphenyl )-8-methyl-1,5-benzothiazepin-4 ( 5H)-one (I-36 )

(37) (2S cis ) 3-hydroxy-5-[3-(4-(2 methoxyphenyl)-1 -piperazinyl)propyl]-2,3-dihydro-2-( 4methoxyphenyl) -8 -chloro- 1,5-benzothiazepin-4 (5H)-one (I-37)

(38) (2R-cis) -3-acetoxy-5-[3-(4-(2 -methoxyphenyl)-1-piperazinyl)propyl]-2,3-dihydro-2-(4 methoxyphenyl)-8-chloro-1,5-benzothiazepin-4(5H)-one (I-38)

(39) (2S-trans)-3-acetoxy-5-[3-(4-(2 -methoxyphenyl)-1-piperazinyl)propyl]-2,3-dihydro-2-(4 -methoxyphenyl)-8-chloro-1,5-benzothiazepin-4(5H)-one (I-39)

The chemical structures and yields of the above compounds except for compound I-1 and 1-17 are listed in Table 1, and the detailed reaction conditions are summarized in Table 2. In addition, Table 3 shows physicochemical properties of the aimed product and the solvents used for their recrystallization.

TABLE 1

| Example No. | 1) X: =N—A—R¹ 2) X: =C—(R¹)R² | | z | n | Y | yield (%) I | yield (%) II |
|---|---|---|---|---|---|---|---|
| 2 | 1) A: R¹: | single bond methyl | g | 3 | Cl | 86.6 a | not isolated |
| 3 | 1) A: R¹: | single bond 2-pyridyl | g | 3 | Cl | 80.5 f | 90.2 |
| 4 | 1) A: R¹: | single bond o-methoxyphenyl | g | 3 | H | 81.0 a | 89.8 |
| 5 | 1) A: R¹: | —CH₂— 3,4-methylenedioxyphenyl | g | 3 | Cl | 98.3 f | 77.1 |
| 6 | 1) A: R¹: | —CH₂— 3,4-methylenedioxyphenyl | g | 3 | Cl | 96.0 a | 41.9 |
| 7 | 1) A: | —CO— | g | 3 | Cl | 64.5 f | 98.0 |

TABLE 1-continued

| Example No. | 1) X: =N—A—R¹ 2) X: =C—(R¹)R² | | z | n | Y | yield (%) I | yield (%) II |
|---|---|---|---|---|---|---|---|
| 8 | 1) A: R¹: | single bond 2-furyl o-methoxyphenyl | g | 3 | Cl | 99.3 f | 84.5 |
| 9 | 1) A: R¹: | single bond phenyl | g | 2 | Cl | 20.3 a | not isolated |
| 10 | 1) A: R¹: | single bond o-methoxyphenyl | g | 2 | Cl | 21.3 a | not isolated |
| 11 | 2) A: R²: | phenyl H | g | 2 | Cl | 21.1 f | not isolated |
| 12 | 1) A: R¹: | single bond p-fluorophenyl | g | 3 | Cl | 96.3 a | 81.1 |
| 13 | 1) A: R¹: | single bond p-fluorophenyl | g | 2 | Cl | 22.3 a | not isolated |
| 14 | 2) R¹: R²: | phenyl phenyl | g | 3 | Cl | 99.0 a | 87.4 |
| 15 | 1) A: R¹: | single bond 4,4'-difluorobenzhydryl | g | 3 | Cl | 85.3 a | 91.4 |
| 16 | 1) A: R¹: | single bond 4-chlorobenzhydryl | g | 3 | Cl | 99.0 a | 77.1 |
| 18 | 1) A: R¹: | single bond o-methoxyphenyl | g | 3 | Cl | 46.2 a | 92.7 |
| 19 | 1) A: R¹: | single bond o-methoxyphenyl | g | 3 | Cl | 82.2 b | 92.7 |
| 20 | 1) A: R¹: | single bond o-methoxyphenyl | g | 3 | Cl | 81.5 c | 92.7 |
| 21 | 1) A: R¹: | single bond o-methoxyphenyl | g | 3 | Cl | 84.7 d | 92.7 |
| 22 | 1) A: R¹: | single bond 4-chlorobenzhydryl | g | 3 | Cl | 74.5 e | 73.0 |
| 23 | 1) A: R¹: | single bond benzhydryl | g | 3 | Cl | 59.8 a | 68.8 |
| 24 | 1) A: R¹: | single bond 4,4'-dichlorobenzhydryl | g | 3 | Cl | 85.1 a | 71.9 |
| 25 | 1) A: R¹: | single bond 4-chlorophenyl | g | 3 | Cl | 78.6 e | 65.7 |
| 26 | 1) A: R¹: | single bond 4-methylphenyl | g | 3 | Cl | 65.7 d | 94.7 |
| 27 | 1) A: R¹: | single bond cyclohexyl | g | 3 | Cl | 71.1 e | 98.2 |
| 28 | 1) A: R¹: | single bond o-methylphenyl | g | 3 | Cl | 58.0 | 79.0 |
| 29 | 1) A: R¹: | single bond p-methoxyphenyl | g | 3 | Cl | 80.0 c | 79.0 |
| 30 | 1) A: R¹: | single bond 2,4-dimethoxyphenyl | g | 3 | Cl | 77.0 f | not isolated |
| 31 | 1) A: R¹: | single bond 3,4-dimethoxyphenyl | g | 3 | Cl | 64.0 | not isolated |
| 32 | 1) A: R¹: | single bond 3,4,5-trimethoxyphenyl | g | 3 | Cl | 55.0 | not isolated |
| 33 | 1) A: R¹: | single bond o-methoxyphenyl | g | 4 | Cl | 75.2 | 84.6 |

TABLE 1-continued

| Example No. | 1) X: =N—A—R¹ 2) X: =C—(R¹)R² | | z | n | Y | yield (%) I | yield (%) II |
|---|---|---|---|---|---|---|---|
| 34 | 1) A: R¹: | single bond o-methoxyphenyl | g | 5 | Cl | 92.1 a | 91.9 |
| 35 | 1) A: R¹: | single bond o-methoxyphenyl | g | 3 | CH₃O— | 88.0 a | 85.0 |
| 36 | 1) A: R¹: | single bond o-methoxyphenyl | g | 3 | CH₃— | 93.0 a | 94.0 |
| 37 | 1) A: R¹: | single bond o-methoxyphenyl | h | 3 | Cl | — | 85.5a |
| 38 | 1) A: R¹: | single bond o-methoxyphenyl | g | 3 | Cl | 69.8 | 84.7 |
| 39 | 1) A: R¹: | phenyl single bond o-methoxyphenyl | g | 3 | Cl | 47.0 c | not isolated | a: hydrochloride
b: phosphate
c: citrate
d: fumarate
e: maleate
f: oxalate
g: acetyl
h: hydrogen

TABLE 2

(Step 1)

| Example No. | Starting Compound mg(mmol) | | Solvent (ml) | Potassium Iodide mg(mmol) | Reaction Temperature (°C.) | Reaction Time (hour) |
|---|---|---|---|---|---|---|
| | Comp.(III) | Comp.(IV) | | | | |
| 2 | 412(1) | 301(3) | i | 5 | 33(0.2) | 83 | 24 |
| 3 | 412(1) | 326(2) | i | 5 | 166(1) | 83 | 16 |
| 4 | 270(0.71) | 275(1.43) | i | 5 | 24(0.15) | 83 | 19 |
| 5 | 412(1) | 440(2) | i | 5 | 166(1) | 83 | 16 |
| 6 | 1340(3.25) | 1340(6.50) | i | 14 | 108(0.65) | 83 | 15 |
| 7 | 412(1) | 360(2) | i | 5 | 166(1) | 83 | 16 |
| 8 | 412(1) | 384(2) | a | 4 | 166(1) | 82 | 16 |
| 9 | 797(2) | 2600(16) | a | 8 | — | 40 | 96 |
| 10 | 398(1) | 461(2.4) | i | 4 | 50(0.3) | 83 | 16 |
| 11 | 398(1) | 387(2.4) | a | 4 | 50(0.3) | 40 | 16 |
| 12 | 341(0.83) | 307(1.7) | a | 6 | 28(0.17) | 82 | 10 |
| 13 | 398(1) | 433(2.4) | i | 4 | 50(0.3) | 83 | 16 |
| 14 | 283(0.69) | 326(1.37) | i | 4 | 23(0.14) | 83 | 19 |
| 15 | 310(0.75) | 433(1.5) | i | 6 | 25(0.15) | 83 | 20 |
| 16 | 412(1) | 574(2) | i | 5 | 166(1) | 83 | 16 |

(Step 1)

| Example No. | Starting Compound mg(mmol) | | Solvent (ml) | Potassium Iodide mg(mmol) | Reaction Temperature (°C.) | Reaction Time (hour) | Potassium Carbonate mg(mmol) |
|---|---|---|---|---|---|---|---|
| | Comp.(III) | Comp.(IV) | | | | | |
| 18 | 412(1) | 384(2) | a | 4 | 166(1) | 82 | 16 | — |
| 19 | 412(1) | 384(2) | a | 4 | 166(1) | 82 | 16 | — |
| 20 | 412(1) | 384(2) | a | 4 | 166(1) | 82 | 16 | — |
| 21 | 412(1) | 384(2) | a | 4 | 166(1) | 82 | 16 | — |
| 22 | 412(1) | 574(2) | i | 8 | 166(1) | 83 | 20 | — |
| 23 | 412(1) | 505(2) | i | 8 | 33(0.2) | 83 | 21 | — |
| 24 | 412(1) | 642(2) | i | 8 | 33(0.2) | 83 | 20 | — |
| 25 | 412(1) | 539(2) | i | 8 | 33(0.2) | 83 | 21 | — |
| 26 | 412(1) | 498(2) | d | 8 | 332(2) | 100 | 3 | — |
| 27 | 412(1) | 337(2) | d | 8 | 332(2) | 100 | 3 | — |
| 28 | 2060(5) | 1270(6) | d | 5 | 1250(7.5) | 100 | 1 | 1650(12) |
| 29 | 1030(2.5) | 793(3)b | d | 5 | 625(3.8) | 100 | 1.5 | 1240(9) |
| 30 | 1030(2.5) | 776(3)b | d | 5 | 625(3.8) | 100 | 2 | 825(6) |
| 31 | 1440(3.5) | 1200(4.2)b | d | 10 | 875(5.3) | 100 | 2 | 825(6) |
| 32 | 2060(5) | 1580(5.5)b | d | 10 | 1250(7.5) | 100 | 2 | 1510(11) |
| 33 | 613(1.44) | 395(1.73) | d | 6 | 239(1.4) | 100 | 2 | — |
| 34 | 642(1.46) | 400(1.75) | d | 6 | 242(1.46) | 100 | 2 | — |
| 35 | 490(1.2) | 460(2.4) | d | 10 | 400(2.4) | 100 | 2.5 | — |
| 36 | 340(0.87) | 335(1.74) | d | 7 | 289(1.74) | 100 | 2.5 | — |
| 37 | 412(1) | 384(2) | a | 4 | 166(1) | 82 | 16 | — |
| 38 | 1120(2.7) | 652(2.9) | d | 5.6 | 451(2.7) | 100 | 2 | — |
| 39 | 1120(2.7) | 652(2.9) | d | 5.6 | 451(2.7) | 100 | 2 | — |

Step 3

TABLE 2-continued

| Example No. | Starting Compound mg(mmol) Comp.(II) | Ac$_2$O (ml) | Reaction Temperature (°C.) | Reaction Time (hour) | Base mg (mmol) |
|---|---|---|---|---|---|
| 2 | 280(0.58) | 5 | 110 | 3 | |
| 3 | 486(0.90) | 4.9 | 100 | 3 | |
| 4 | 342(0.64) | 3.4 | 100 | 3 | |
| 5 | 400(0.67) | 3 | 100 | 3 | |
| 6 | 792(1.36) | 8 | 100 | 3 | |
| 7 | 878(1.58) | 8.8 | 100 | 3 | |
| 8 | 400(0.71) | 10 | 100 | 3 | |
| 9 | 619(1.18) | 6.2 | 100 | 3 | |
| 10 | 159(0.29) | 1.6 | 100 | 3 | |
| 11 | 283(0.54) | 2.3 | 100 | 3 | |
| 12 | 800(1.44) | 10 | 110 | 4 | |
| 13 | 163(0.3) | 1.6 | 100 | 3 | |
| 14 | 361(0.6) | 3.6 | 100 | 3 | |
| 15 | 456(0.69) | 4.5 | 100 | 2.5 | |
| 16 | 480(0.72) | 6 | 100 | 4 | |
| 18 | 400(0.71) | 10 | 100 | 3 | |
| 19 | 400(0.71) | 10 | 100 | 3 | |
| 20 | 400(0.71) | 10 | 100 | 3 | |
| 21 | 400(0.71) | 10 | 100 | 3 | |
| 22 | 483(0.73) | 4.8 | 100 | 4 | |
| 23 | 432(0.69) | 4.3 | 100 | 3 | |
| 24 | 501(0.72) | 5 | 100 | 3 | |
| 25 | 376(0.66) | 2 | 30 | 21 | |
| 26 | 523(0.95) | 2.7 | 30 | 13 | |
| 27 | 534(0.98) | 5 | 30 | 14 | |
| 28 | 2040(3.7) | 10 | 30 | 15 | m 22(0.18) |
| 29 | 1640(2.66) | 5 | 30 | 15 | m 20(0.17) |
| 30 | 1500(2.5) | 5 | 30 | 48 | m 20(0.17) |
| 31 | 2030(3.39) | 7 | 30 | 2 | m 30(0.24) |
| 32 | 3140(5.0) | 8 | 30 | 2 | m 23(0.18) |
| 33 | 708(1.22) | 7 | 30 | 4 | m 7.5(0.06) |
| 34 | 799(1.34) | 8 | 30 | 4 | m 7.5(0.06) |
| 35 | 570(1.01) | 5.7 | 40 | 16 | p 100(1.26) |
| 36 | 330(0.6) | 3.3 | 30 | 1 | m 20(0.06) |
| 37 | — | — | — | — | — |
| 38 | 1307(2.3) | 6.5 | 30 | 16.5 | m 14.1(0.12) |
| 39 | 1245(2.2) | 6.2 | 30 | 16 | m 13.4(0.11) | a: acetonitrile
i: isopropanol
d: dimethylformamide
b: hydrochloride
m: dimethylaminopyridine
p: pyridine

TABLE 3

| Exam. No. | Appearance | Recrystallization Solvent | MP(°C.) | Specific Rotation $[\alpha]^{25}_D$MeOH | IR($v_{max}$cm-1) Nujol |
|---|---|---|---|---|---|
| 2-I a | CP | methanol | 250–252(d) | | 1746,1656 |
| 2-II b | CG | acetone | 230–231 | | 1724,1664 |
| 3-I b | CP | acetone | 142–145 | | 1759,1684 |
| 3-II | oil | — | — | | — |
| 4-I a | CP | acetone | 138–140 | | 1732,1687 |
| 4-II | CG | hexane | 75–76 | | 1662 |
| 5-I b | YG | methanol | 212–214(d) | | 1745,1685 |
| 5-II | oil | — | — | | 1661 |
| 6-I a | CP | acetone | 160–162 | | 1737,1677 |
| 6-II | oil | — | — | | — |
| 7-I b | CP | acetone | 196–197 | | 1738,1688 |
| 7-II | oil | — | — | | — |
| 8-I b | CG | acetone | 183–185 | | 1749,1686 |
| 8-II | CP | hexane | 75–76 | | 1662 |
| 9-I b | CP | acetone | 154–156 | | 1742,1683 |
| 9-II | — | — | — | | — |
| 10-I a | YP | acetone | 153–157 | | 1742,1655 |
| 10-II | — | — | — | | — |
| 11-I b | CP | acetone | 141–144 | | 1748,1705 |
| 11-II | — | — | — | | — |
| 12-I a | CN | ethanol/ether | 144–145 | | 1738,1675 |
| 12-II | CP | hexane | 70–71 | | 1664 |

TABLE 3-continued

| Exam. No. | Appearance | Recrystallization Solvent | MP(°C.) | Specific Rotation [α]$^{25}_D$MeOH | IR($\nu_{max}$cm−1) Nujol |
|---|---|---|---|---|---|
| 13-I a | CP | acetone | 153–155 | | 1753,1679 |
| 13-II | — | — | — | | — |
| 14-I a | CP | acetone | 225–230 | | 1746,1678 |
| 14-II | oil | — | — | | — |
| 15-I a | CP | acetone | 157–159 | | 1748,1671 |
| 15-II | oil | — | — | | — |
| 16-I a | CP | acetone | 149–152 | | 1750,1673 |
| 16-II | CP | hexane | 108–109 | | — |
| 18-I a | CP | acetone | 147–150 | +67.9 ± 1.1(c = 1.012) | 3374,2282, 1745,1677 |
| 18-II | oil | — | — | — | |
| 19-I c | CP | methanol | 140–143 | +69.9 ± 1.1(c = 1.005) | 2350,1742, 1680 |
| 20-I d | CP | methanol | 187–189 | +65.0 ± 1.0(c = 1.007) | 3430,2620, 1737,1674 |
| 21-I e | CP | ethanol | 115–117 | +69.6 ± 1.1(c = 1.003) | 3276,2506, 1741,1672 |
| 22-I f | CA | ether | — | +56.2 ± (c = 1.015) | 3324,2394, 1744,1678 |
| 22-II | oil | — | — | — | |
| 23-I a | CA | — | — | +64.1 ± 1.0(c = 1.005) | *3410,2392, 1676 |
| 23-II | CA | — | — | — | — |
| 24-I a | CA | — | — | +54.5 ± 0.9(c = 1.003) | *3488,1661 |
| 24-II | oil | — | — | — | |
| 25-I f | CA | — | — | +65.3 ± 1.0(c = 1.014) | *3500,2394, 1744,1678 |
| 25-II | oil | — | — | — | |
| 26-I e | CA | — | — | +73.8 ± (c = 1.009) | 3428,2606, 1743,1677 |
| 26-II | oil | — | — | — | — |
| 27-I f | CP | ethanol | 195–202 | +73.9 ± 1.1(c = 1.013) | 3260,2348, 1752,1685 |
| 27-II | oil | — | — | — | |
| 28-I | CP | ethanol | 187–188 | +110.8 ± 1.5(c = 1.006) | — |
| 28-II | oil | — | — | — | |
| 29-I d | CP | ethanol | 197–198 | +58.8 ± 1.0(c = 1.004) | — |
| 29-II | oil | — | — | — | — |
| 30-I b | CP | ethanol | 175–176 | +66.8 ± 1.1(c = 1.01) | — |
| 30-II | oil | — | — | — | — |
| 31-I | CP | ethanol | 170–171 | +101.8 ± (c = 1.011) | — |
| 31-II | oil | — | — | — | |
| 32-I | CP | ethanol | 162–163 | +93.9 ± 1.3(c = 1.016) | — |
| 32-II | oil | — | — | — | |
| 33-I | CP | hexane | 139–140 | +90.9 ± 1.3(c = 1.013) | 1743,1676 |
| 33-II | oil | — | — | — | |
| 34-I a | CA | — | — | +76.2 ± 1.2(c = 1.008) | *3486,2390, 1739,1676 |
| 34-II | CA | — | — | — | — |
| 35-I a | CA | — | — | +70.1 ± 1.1(c = 1.003) | — |
| 35-II | oil | — | — | — | |
| 36-I a | CA | — | — | +80.5 ± 1.2(c = 1.005) | — |
| 36-II | oil | — | — | — | |
| 37-II a | CP | acetone | 135–137 | +83.8 ± 1.2(c = 1.007) | 3380,2360, 1660 |
| 38-I | CP | hexane | 109–111 | −110.1 ± 1.5(c = 1.018) | 1746,1678 |
| 38-II | CN | hexane | 175–178 | — | — |
| 39-I d | CP | methanol | 191–192 | +275.8 ± 3.1(c = 1.018) | 3446,2542, 1736,1640 |
| 39-II | oil | — | — | — | — | a: hydrochloride
b: oxalate
c: phosphate
d: citrate
e: fumarate
f: maleate
*: in chloroform
CP: colorless prisms
YG: yellow granular crystal
YP: yellow prisms
CN: colorless needles
CA: colorless amorphous Following pharmacological experiments were conducted on the compounds (I) of the invention.

EXPERIMENT 1

Calcium Channel Antagonism and Q-Blocking Action (Relaxing Action on Extracted Blood Vessel)

Male rabbits weighing 2–3 kg (Rabiton, Japanese albino species) were anesthetized through intravenous administration of pentobarbital (50 mg/kg), and sacrificed by bloodletting through dissection of axillary artery. Femoral artery was extracted, connective tissue surrounding the artery was removed, and helical specimen was prepared. The specimen was suspended in an organ bath (20 cc) filled with 37° C. Krebs-Henseleit nutritious solution and bubbled with a 95% $O_2$+5% $CO_2$ mixed gas. 1.5 g of resting tension was loaded on femoral artery. Isometric change of the tension of the specimen was recorded on a thermal recorder (Nippon Koden WT-685G) via F-D pickup Nippon Koden (TB611T) and Preamp (Nippon Koden). Ca-antagonism of a test compound was evaluated by observing relaxing action due to accumulative addition of the compound on the contracture caused by the application of 50 mM KCl. α-Blocking action was similarly evaluated by observing such relaxing action on the contracture caused by the application of 1 μM norepinephrine (NE). Maximum relaxing ability possessed by the blood vessel was defined as the same as relaxing response of the vessel observed when 0.1 mM of papaverine was applied. The concentration of a given compound, which is necessary for giving 50% of the maximum relaxing ($IC_{50}$), was determined using the above system. The results are shown in Table 4.

TABLE 4

| Compound No. | Relaxing action on Blood Vessel $IC_{50}$(x0.1 μm) | |
|---|---|---|
| | 50mM-KCl | 1 μM-NE |
| I-5 | 2.5 | |
| I-8 | 2.8 | 0.6 |
| I-11 | 2.0 | |
| I-14 | 1.0 | |
| I-15 | 0.57 | 6.0 |
| I-16 | 2.4 | |
| I-18 | 2.5 | 0.37 |
| I-22 | 3.4 | |
| I-35 | 1.2 | 0.3 |
| I-36 | 1.4 | 0.2 |
| Diltiazem | 4.2 | 133 |

EXPERIMENT 2

Anti-hypoxia action on cultured cardiac cells

Anti-hypoxia action of the compounds of the present invention were investigated through studying their action in connection with the protection of cardiomuscular cells.

Primary culture of cardiac cells was prepared from newborn Crj-SD rats (2–3 day old) and used in the experiment. The primary culture was prepared according to the method described by Jones R. L. et al., Am. J. Pathol., 135, 541–556, 1989. Thus, cardiac cells were isolated from ventricle muscle using collagenase and pancreatin, and then the cardiac cells were separated and purified from cell debris, erythrocytes, and fibroblasts by means of Percoll density-gradient centrifugation. The cells were spread on a culture plate at a ratio of 2–3×10⁵ cells/3.5 cm plate, and the cells were cultured for two days in Dulbecco's Modified Eagle's Medium (DMEM) containing 10% Fetal Bovine Serum (FBS) in an incubator (5% $CO_2$/95% Air) kept at 37° C. After sufficient growth of the cardiac cells, the culture medium was changed to DMEM free from FBS, and the culture was continued additional one day. The cells thus obtained were used in the experiment.

Hypoxia was generated using Gas Pak™ Anaerobic Chamber (BBL) which produces hypoxia by capturing residual $O_2$ and changing it into $H_2O$ by the action of a $H_2/CO_2$ generating bag and catalyst. The cardiac cell plate, wherein the culture medium had been changed to DMEM which is free from FBS and glucose, was set in the chamber, and the chamber was placed in an incubator. Anti-hypoxia activity of test compounds was determined by measuring inhibition rate of leakage of creatine phosphokinase activity into the culture medium.

The compounds tested were all dissolved in DMSO using HCO-50 as a solubilizing agent (DMSO:HCO-50=9:1), and directly charged onto the culture plate. The final concentrations of DMSO and HCO-50 in the culture medium were adjusted to 0.09% and 0.01% respectively. CPK activity was measured by colorimetry (Wako Kit) modified from Oliver method. The test results are summarized in Table 5.

TABLE 5

| Compound No. | Anti-hypoxia 1 μM | Activity (%) 10 μM |
|---|---|---|
| I-1 | — | 66 |
| I-3 | 34 | |
| I-5 | — | 66 |
| I-7 | 36 | |
| I-8 | 17 | 70 |
| I-12 | 10 | 87 |
| I-13 | 15 | 61 |
| I-14 | — | 83.6 |
| I-15 | — | 76 |
| I-16 | 18.4 | 57 |
| I-18 | 23.7 | 73.9 |
| I-22 | 25.7 | 73.9 |
| I-23 | 36.4 | 87 |
| I-24 | 14.1 | 88 |
| I-25 | 25.2 | 89 |
| I-29 | 30 | |
| I-32 | — | 66.1 |
| I-33 | 36.9 | 87 |
| I-34 | — | 80.0 |
| Diltiazem | 10 | 29 |

The numerical values in the table show cardiac cells-protecting activity of test compounds in terms of the rate (%) of inhibition on CPK leakage determined in connection with the test compounds when the amount of the CPK leakage for negative control (no addition of the test compounds) was defined as 100%. Table 5 clearly shows that the compounds of the present invention display higher protecting activity than the positive control (diltiazem).

EXPERIMENT 3

Action of the compounds of the invention on blood pressure and heart rate of not-anesthetized spontaneous hypertensive rats (SHR)

Male Japanese Charles-River SHR (13–17 week old) were used in the experiment (S. Matsuda, J. Pharmacol. Method, 17 361, 1987). Systolic blood pressure (SBP) and heart rate of the animals were measured non-invasively (indirectly) using hemadynamometer for caudal artery pressure (6 channel type) before the administration of test compounds, at 2 and 4 hours after administration. Test compounds were dissolved in DMSO (100%) and orally administered. Decreased values in SBP and heart rate determined 2 and 4 hours after administration when compared with those determined before administration are shown in percentage (%) in the following table.

TABLE 6

| Compound No. (30mg/kg PO) | Antihypertensive action (%) | Decrease of heart rate (%) |
|---|---|---|
| I-8 | 15 | 3.2 |
| I-14 | 14 | 9.8 |
| I-15[a] | 17 | 6.5 |
| I-16 | 19 | 15 |
| I-18 | 18 | 7.0 |
| I-22 | 18 | 9.4 |
| I-23 | 16 | 12 |
| Diltiazem[a] | 11 | 15 |

[a]: 60 mg/kg PO

EXPERIMENT 4

Anti-necrosis Activity

Male Sic Wistar rats weighing 200–250 g were anesthetized with urethane (1 g/kg), and ramus descendens of the left coronaria was ligated for 20 minutes and then reperfused according to the method described by Hock et al (Hock, C. E., Ribeiro, L. G., Tand Lefer, A. M., Am. Heart J., 109 222, 1985). Compounds to be tested were dissolved in physiological saline, or first dissolved in a DMSO/HCO-(50 (9:1) mixture and then diluted with physiological saline or 0.25M aqueous sucrose solution, and infused into the right cervical vein at a ratio of 0.15 ml/kg/minute for ten minutes before the ligation. For three hours after the reperfusion, the rats were subjected to heat insulation on a warming mat. After 120 minutes, the hearts were extracted, and the free walls of the left ventricles were frozen and storred until determination of CPK activity.

CPK activity was determined according to the method of Bernauer, W. (Arch. int. Pharmacodyn., 231 90, 1978) after minor modification. Thus, the extracted tissue was homogenized in 10 volumes of 0.1M Tris/HCl (pH 7.5) containing 1 mM mercaptoethanol and centrifuged at 20,000 g for 20 minutes. The supernatant was used for determination of CPK activity, which was conducted using a commercially available kit (CPK-Test, Wako). CPK was determined using serum CPK as a standard and expressed with "U/mg protein".

The inhibition of cardiac muscle damage due to ischemia, which should be obtained when a test compound is administered, was compared with the inhibition obtained when an active control, diltiazem, was administered. The degree of the inhibition was measured in terms of the CPK activity retained in the left ventricle. The test results are shown in Table 7, wherein percentage of the retention (%) at each dose was calculated based on the following equation. Retention (%)=[(Retained CPK activity when a test compound was administered)-(Retained CPK activity when only a medium was administered)]/[(CPK activity possessed by intact animals)-(Retained CPK activity when only a medium was administered)]

TABLE 7

| | | (anti-necrosis activity) | |
| Compound No. | Retention (%) 0.1 | mg/kg (iv) 0.3 | 1 |
|---|---|---|---|
| I-8 | | 29 | |
| I-12 | | | 23 |
| I-18 | 30 | 42 | |
| I-22 | | 45 | |
| I-23 | | 45 | |
| I-24 | | 35 | |
| I-35 | | | 37 |
| I-36 | | | 30 |
| Diltiazem | | | 13 |

What is claimed is:

1. A compound of the formula

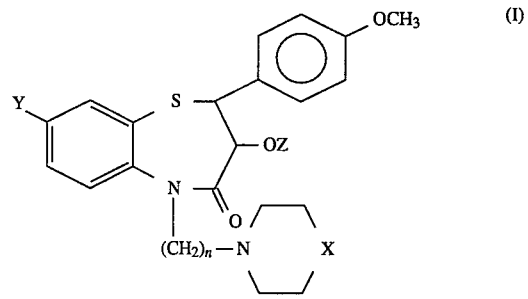

wherein X is =NR[1]; R[1] is optionally substituted benzhydryl; Y is hydrogen, halogen, $C_{1-6}$ alkyl or $C_{1-6}$ alkoxy; Z is hydrogen or acetyl; n is an integer of from 3 to 6, or a pharmaceutically acceptable salt thereof.

2. A compound as claimed in claim 1, wherein Y is chloro; and n is 3.

3. A compound as claimed in claim 2, wherein Z is acetyl.

4. A compound as claimed in claim 2, wherein Z is hydrogen.

5. A compound as claimed in claim 2, wherein R[1] is benzhydryl substituted by halogen.

6. A compound as claimed in claim 3, wherein R[1] is benzhydryl substituted by halogen.

7. A pharmaceutical composition which comprises a pharmaceutically effective amount of a compound of claim 1 in association with a pharmaceutically acceptable carrier or excipient.

8. A method for the treatment of hypertension which comprises administering an effective amount of a compound of claim 1 to a human being or animal.

9. A method for the treatment of ischemic disease which comprises administering an effective amount of a compound of claim 1 to a human being or animal.

* * * * *